United States Patent [19]

Felix

[11] 4,282,231
[45] Aug. 4, 1981

[54] BIOCIDAL MERCAPTOPYRIDINE HALOACRYLYLNITRILE COMPOUNDS

[75] Inventor: Raymond A. Felix, Richmond, Calif.

[73] Assignee: Stauffer Chemical Company, Westport, Conn.

[21] Appl. No.: 172,356

[22] Filed: Jul. 25, 1980

[51] Int. Cl.³ .................. C07D 213/57; A0IN 43/40
[52] U.S. Cl. .................................. 424/263; 546/300
[58] Field of Search ...................... 546/300; 424/263

[56] References Cited
U.S. PATENT DOCUMENTS 3,138,606  6/1964  Scotti et al. ........................ 546/300
4,238,405  12/1980  Felix ................................... 260/464

Primary Examiner—Alan L. Rotman

[57] ABSTRACT

Novel biocidal compounds having the general structural formula

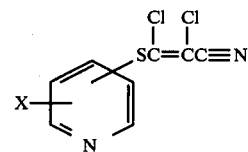

wherein X is selected from the group consisting of —H, halogen, including —Br, —Cl and —F, $C_1$-$C_4$ alkyl, including methyl, ethyl, propyl and butyl.

6 Claims, No Drawings

BIOCIDAL MERCAPTOPYRIDINE HALOACRYLYLNITRILE COMPOUNDS

BACKGROUND OF THE INVENTION

Various 1,2-dichlorocyanovinyl compounds are disclosed in the prior art as having antimicrobial properties. Many of these compounds are disclosed in co-pending U.S. patent application Ser. No. 834,215, filed Sept. 19, 1977 now U.S. Pat. No. 4,238,405. Compounds disclosed are those having the general structural formula

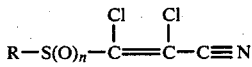

wherein n is 0, 1, or 2 and R is selected from the group consisting of alkyl, alkylcarbalkoxy, cyclohexyl, halophenyl, benzyl, N,N-di-lower alkyl carbamoyl, hexamethyleneimino carbonyl, pyrimidyl, lower alkyl substituted pyrimidyl, benzimidazole, lower alkyl substituted imidazole, benzothiazole and O,O-di-lower alkyl thiophosphoryl; with the proviso that when n is O, R is other than alkyl or cyclohexyl.

DESCRIPTION OF THE INVENTION

This invention relates to novel biocidal 1,2-dichlorocyanovinyl sulfide compounds. The novel compounds of this invention have the general structural formula

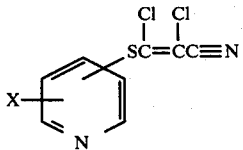

wherein X is selected from the group consisting of —H, halogen, including —Br, —Cl and —F, $C_1$-$C_4$ alkyl, including methyl, ethyl, propyl and butyl.

The compounds are prepared by reacting trichloroacrylyl chloride with aqueous ammonia at a temperature of about −30° C. to about 100° C., preferably about 0° C. to about 20° C., to form trichloroacrylylamide. The trichloroacrylylamide is then dehydrated using a dehydrating agent such as, for example, phosphoryl chloride, phosphorus pentoxide, trifluoroacetic anhydride, pyridine or thionyl chloride. The resulting trichloroacrylylnitrile is reacted with a mercaptan having the formula

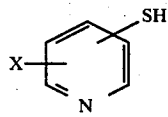

wherein X is as defined above in the presence of an acid acceptor, such as, for example, triethylamine, potassium t-butoxide, sodium methoxide, or a phase transfer catalyst with sodium hydroxide, for example, benzyl triethylammonium chloride and sodium hydroxide, to form the desired sulfide. The sulfoxide and sulfone derivatives are formed by reacting the sulfide with an oxidizing agent such as hydrogen peroxide or organic peracids, such as peracetic acid, performic acid, or m-chloroperoxybenzoic acid. The resulting product is a cis-trans-isomer mixture of the 1,2-dichlorocyanovinyl compound. Separation of the isomers can be effected by standard procedures, if desired, but is not necessary for utilization of these compounds as biocides.

This preparation can be illustrated by the following equations:

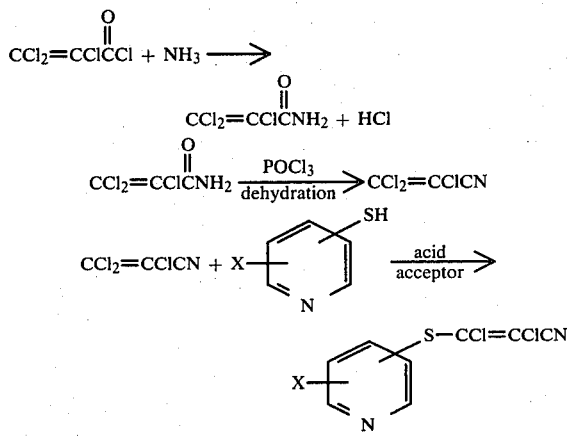

The novel compounds of this invention are biocides in that they prevent, control or inhibit the growth of microorganisms selected from bacteria and fungi. Thus, another embodiment of this invention comprises a method of controlling microorganisms selected from bacteria and fungi by applying to the locus where such control is desired an effective amount of the novel compounds described above. Some of the compounds of this invention are particularly useful as soil fungicides, controlling the growth of fungi when incorporated into soil. The effective amount of the particular compound used will vary depending on the degree of control desired. Generally, about 0.5 to about 6 pounds per acre, preferably about 1 to about 4 pounds per acre, will be employed. When used as a foliar fungicide to protect vegetation from fungus growth, about 0.5 to about 6, preferably about 1 to about 4 pounds of compound dissolved or dispersed in 100 gallons of water should be sprayed on the foilage to be protected. For other uses of the compounds of this invention to control microorganisms, one skilled in the art will be able, without undue experimentation, to determine the effective amount of the compound required to provide the desired degree of control.

The following example illustrates the preparation of typical compounds of this invention and demonstrates their utility as biocides.

EXAMPLE I

2-(2-Cyanodichlorovinylmercapto)Pyridine 0.026 mole (m) (2.9 grams (g)) of 2-mercaptopyridine was dissolved in 15 milliliters (ml) of $CH_2Cl_2$ and 0.026 m (4.1 g) of trichloroacrylylnitrile was added. The mixture was then cooled in an ice bath. 0.029 m (4.0 ml) triethylamine was then added to the mixture which was then stirred at room temperature overnight. The product was recovered by adding an additional 50 ml of $CH_2Cl$ to the reaction mixture and washing the reaction mixture with $H_2O$. The organic layer was separated and dried over $MgSO_4$ as a desiccant. The solvent was then evaporated to recover the title compound which was analyzed by nuclear magnetic resonance, infrared spectra and mass spectroscopy identifying the reaction product as the title compound, having the formula

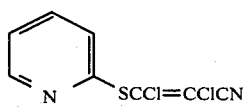

As stated above, the novel compounds of this invention are biocides. The compound of Example I was tested for bacterial and fungicidal activity using the following test procedures.

Toxicity Tests on Bacteria, Yeast and Fungal Spores

A. Preparation of Original Cultures

The following cultures are grown on a shaker for 18–24 hours for use in the screening procedure:

1. *Klebsiella pneumoniae* (Institute for Paper Chemistry (IPC)-500) in Tryptisase Glucose Extract (TGE) broth at 37° C.
2. *Bacillus megaterium* (ATCC-14581) in TGE broth at 30° C.
3. *Pseudomas aeruginosa* (ATCC-10145) maintain on nutrient augar at 37° C.
4. The fungal spores of *Trichoderma viride* are prepared by inoculating 50 ml portions of Sporulation Medium (V-8 juice 200 ml, $CaCO_3$ 2 g, augar 20 g, distilled water 800 ml). Sporulation is achieved after 6–8 days incubation at 30° C.

B. Preparation of Inocula

The overnight cells from the bacterial and yeast cultures are centrifuged at 10,000 g for 10 minutes (Sorvall RC-5) and the supernatant media discarded. The cell pellets are resuspended in Wilson's Salts Medium ($K_2HPO_4$ 3 g, $KH_2PO_4$ 1.5 g, $MgSO_4$ 0.1 g, $(NH_4)_2SO_4$ 1.0 g, $H_2O$ 1 liter: final pH 7) and adjusted to 150 Klett Units turbidity. Fifty (50) µl aliquots of these cultures are added to Microtiter plate wells designated for each of the organisms.

The fungal spores are harvested by washing the surface of Sporulation Medium with 10 ml Wilson's Salts Medium 5% Dextran. The resulting suspension, which is 90–95% spores, is adjusted to 150 Klett Units by the addition of fresh Wilson's (5% Dextran) Medium. Fifty (50) µl portions are used in the Microtiter System.

C. Preparation of Biocides

Toxicant concentrations in the wells are achieved by adding 25 µl portions to each of the wells from toxicant stock solutions made to the appropriate concentration in Wilson's Medium. Where organic solvents, such as, isopropyl alcohol, ethyl alcohol, acetone or dimethyl sulfoxide, are required to render an acceptable solution, the concentration of solvent is to be kept at a minimum and must be kept below 1% maximum safe level. A control for each organism (no biocide addition) was achieved by adding 25 µl of Wilson's Medium to an appropriate series of wells instead of the toxicant addition.

D. Preparation of Isotope

The assay material (labeled substrate) is $^{14}C$ D-Glucose (U) from New England Nuclear. The concentrated solution (1–5 mCi/m mol; 50 uCi/5 ml) was diluted to the use concentration 1 uCi/ml in Wilson's Medium. Twenty-five (25) µl volumes of this stock solution were added to each well of the Microtiter plate.

E. Microtiter Procedure

A clean plastic Microtiter "U" plate (Cooke Laboratories) was placed on damp paper towels to minimize static charge (a charged plate will pull uneven drops from the Microtiter pipets, thus affecting test results). A series of wells was prepared in the following order to each toxicant concentration:

1. Each well received 25 µl of toxicant at four times the desired final concentration to achieve a correct level per 100 µl (one series receives 25 µl of Wilson's Medium-no toxicant-and acts as the controls and duplicate positive controls utilizing methylene bisthiocyanate at 5 µg/ml are also included against each organism, thus assuring the validity of the assay). Methylene Bisthiocyanate (MBT) is a toxicant giving accurate and repeatable $I_{50}$ values.
2. Twenty-five (25) µl of the 1 uCi/ml solution of $^{14}C$ D-Glucose (U) was added to the appropriate test wells.
3. Fifty (50) µl of the appropriate cell suspension was added to the wells which correspond to that organism to begin the test. Wells containing samples were then covered with scotch tape until sampling time to prevent excessive evaporation. Samples were taken after 120 minutes. The Microtiter plate is incubated at 30° C. during the test procedure. Due to the rapidity of the test (2 hours), sterility was maintained up to the final additions to the Microtiter plate but the test need not remain under aseptic conditions during the course of the experiment.

Samples at each biocide concentration were always run in duplicate. The 25 µl and 50 µl additions were made with Microdropper pipets (Cooke laboratories, Alexandria, Va.) manufactured to give drops of those two sizes.

F. Sampling Technique-Titertek Multisampler

The Titertek Multisampler is designed to simultaneously extract and flush the entire contents from 12 Microtiter test wells (a row) through 12 specific areas on a Skatron fiberglass filter. The larger $^{14}C$ labeled organisms (*T. viride spores*) are readily entrapped by the filters and the results are comparable to the much slower Millipore filtration technique. However, the smaller organisms (*K. pneumoniae, B. megaterium* and *P. aerugenosa* pass through the filter. When 100 µl of a 400 µg/ml solution of the low molecular weight cationic Polymer 1185 (final concentration 200 µg/ml) was added to each of the wells immediately before sampling of the smaller organisms, good to excellent cell retention (results also comparable to the Millipore Procedure) was achieved. After the filters were air dried, the sample spots are easily punched out of the filter mat and placed in scintillation vials containing 10 ml Aquasol II (new England Nuclear) for counting on the Beckman LS-3133T) for 10 minutes (or 10,000 counts). Channel settings of the liquid scintillation counter were optimized for $^{14}C$. Background values and quenching were checked after each run to insure accurate and reproducible results.

G. Interpretation of Test Results

The amount of $^{14}C$ D-Glucose (U), accumulated by the cells is a time dependent process directly related to the cell concentration. Therefore, which actively growing cells, the cell concentration and accumulation of labeled substrate by the cells will increase over a two hour test period. However, when toxic materials are introduced into the system, cellular activity, growth, and therefore, accumulation of $^{14}C$ will be inhibited. The zero toxicant concentration samples (controls) are used to establish the standard growth of the respective organisms. By evaluating the data from the samples receiving the various concentrations of biocide, one can relate the reduction of $^{14}C$ uptake to the control. A reduction in the $^{14}C$ uptake from that of the control indicate inhibition of cellular activity. MBT controls at 5 μg/ml should give $\geq 50\%$ inhibition or the assay should be considered invalid. The inhibition was measured by an $I_{50}$ value at a specific time. $I_{50}$ value represents the concentration of toxicant in parts per million (ppm) required to decrease the uptake of $^{14}C$ D-Glucose (U) by $\geq 50\%$ when compared with the controls over an identical time period. Chemicals giving $\geq 50\%$ $^{14}C$ D-Glucose uptake inhibition at 50 μg/ml against the listed organisms were considered efficacious.

Radiometric Microscale Bioassay for Aligicides

A. Theory of Assay

This assay utilizes the uptake of radioactively labeled sodium bicarbonate ($^{14}C$) by three representative algae to simulate short-term photosynthesis, and the ability of toxicants to inhibit this process. Algae utilize bicarbonate as their primary carbon source during normal photosynthetic metabolism. Therefore, the inhibition of bicarbonate uptake by toxic materials is a relevant parameter to monitor for showing efficacy of a toxic material. These assays are run in Microtiter plates containing U shaped wells of 225 μl (0.225 ml) volume. Each assay is run in a series of these wells over a period of 4 hours. Positive and negative controls are included. The algae are allowed to incorporate the $^{14}C$-bicarbonate for 4 hours in the presence and absence of these toxic materials. The algal cells are then separated from the medium by filtration and the radioactive cell-containing filters counted by liquid scintillation counting. The bicarbonate uptakes of the algae samples containing toxicant are compared to negative control levels. The % inhibition of sodium bicarbonate uptake was then calculated for each toxicant at the concentrations used.

The concentration of toxicant in ppm which causes a 50% reduction in bicarbonate uptake by the algae is called an $I_{50}$ value. Any material which causes $\geq 50\%$ inhibition of photosynthesis in algal cells at $\leq 100$ μg/ml was considered efficacious.

B. Stock Cultures

1. *Chlorella pyrenoidosa* (University of Texas Culture Collection—formerly Indiana University Culture Collection). Maintained in Bristol's Medium.
2. *Scenedesmus obliquus* (University of Texas Culture Collection). Maintained in Bristol's Medium.

C. Special Equipment

1. Pre-sterilized, individually wrapped Microtiter plates in 96 or 144 U shaped well configurations were used. These were purchased from Cooke Laboratories, Linbro Chemical Company (A/S Nunc, etc.).
2. A Klett-Summerson photometer was used to measure culture turbidities.
3. A Millipore Multisampler (12 sample unit) was used to trap cells. Twenty-five (25) mm, 0.45μ pore filters (Millipore, Amicon, Nucleopore, etc.) were used with the filtration unit.
4. A Liquid Scintillation Counter (Beckman LS-3133T) was used to make $^{14}C$ determinations.
5. Aquasol II (New England Nuclear) scintillation fluid was used in measuring sample activity.
6. $NaHCO_3$ [$^{14}C$] 5-10 mCi/m mole produced by New England Nuclear, Amersham-Searle, etc., was used.

D. Assay Procedure

The assays are conducted using Microtiter plates and Microdropper pipets. The assays are run by placing the following additions (in order given) into Microtiter plate wells. Samples are all run in duplicate.

1. Twenty-five (25) μl addition of toxicant concentrated to give appropriate final concentration in a total volume of 100 μl is added. Final organic solvent concentration must not exceed 1%. Solvent used was isopropanol. Negative controls have 25 μl sterile water replacing the 25 μl toxicant addition.
2. Twenty-five (25) μl $^{14}C$-$NaHCO_3$ solution in sterile $10^{-2}$ M $K_2HPO_4$ is added. A stock isotope solution of 10μ Ci/ml is added to give a final concentration of 0.25 μCi/100 μl.
3. Fifty (50) μl of the appropriate algal cell suspension grown as described above is added.

After all additions have been made, the Microtiter plates were then covered with transparent tape to eliminate loss of sample volume through evaporation. Bicarbonate uptake was allowed to proceed for 4 hours at ambient temperature under saturating lighting conditions provided by continuous illumination from cool-white fluorescent lamps. The tape is then removed, the samples were each stirred and 50 μl removed by Eppendorf pipet. Each 50 μl sample was vacuum filtered through a 0.45μ pore Millipore filter. The filters were washed with 5 ml distilled water and air dried for 10-15 minutes. Each filter was then placed into 10 ml Aquasol 2 liquid scintillation fluid in scintillation vials. The sample vials were then counted in a liquid scintillation counter which has settings optimized for $^{14}C$ counting. The appropriate background counts were then deducted from the experimental values.

E. Controls

Duplicate negative controls were run in which 25 μl sterile distilled water replaces the toxicant addition as stated above. Positive controls were also incorporated into the test by using $CuSO_4.5H_2O$ at 1, 5, 10, 25 and 50 μg/ml. These reference toxicant concentrations bracketed the 50% $^{14}C$-$NaHCO_3$ uptake inhibition values for each algal species to confirm culture susceptibility to toxicants.

F. Interpretation of Results

The duplicate 4 hour bicarbonate uptake controls for each algal species were averaged. Each biocide concentration result was then determined and converted to a % reduction of the bicarbonate uptake using the negative controls as 100%.

The concentration of toxicant which gave a 50% reduction of bicarbonate uptake is called the $I_{50}$ value for that compound. Toxicants having $I_{50}$ values of $\leq 100$ μg/ml are considered efficacious against aglae.

The results of the tests are shown in Table I.

TABLE I

| Biocide | Toxicant I₅₀ Level in PPM | | | | | |
|---|---|---|---|---|---|---|
| | K. pneumoniae | B. megaterium | P. T. aeruginosa | C. viride | S. pyrenoidosa | obliquus |
| Ex. I | 32 | 43 | 13 | 81 | 46 | 55 |

The novel compounds of this invention are generally applied to the locus where control of bacteria or fungi is desired in the form of formulations containing an effective amount of the compound and an inert carrier. Such formulations generally take the form of dusts, wettable powders, solutions, emulsifiable concentrates or the like. Such formulations normally contain up to about 80% by weight of the active ingredient.

Dusts are free-flowing powder compositions containing the active compound impregnated on a particulate carrier. The particle size of the carrier is usually in the range of from about 30 to 50 microns. Examples of suitable carriers are talc, bentonite, diatomaceous earth, and pyrophyllite. Anticaking and antistatic agents can be added, if desired.

Wettable powders are finely divided compositions comprising a particulate carrier impregnated with the active compound and additionally containing one or more surface active agents. The surface active agents promote rapid dispersion of the powder in aqueous medium to form stable, sprayable suspensions. A wide variety of surface active agents can be used, for example, long chain fatty alcohols and alkali metal salts of the sulfated fatty alcohols, salts of sulfonic acid, esters of long chain fatty acids and polyhydric alcohols and the like. A list of surface active agents suitable for use in agriculture formulations can be found in Pesticide Formulations by Wade Van Valkenburg, Marcel Dekker, Inc., N.Y., 1973 at pages 79–84.

Granules comprise the active compound impregnated on a particulte inert carrier having a particle size of 1 to 2 millimeters (mm) in diameter. The granules can be made by spraying a solution of the active ingredient in a volatile solvent onto the granular carrier. Suitable carriers in preparation of granules include clay, vermiculite, sawdust, granular carbon, and the like.

The active compounds can also be applied in the form of a solution in a suitable solvent. Solvents frequently used in biocidal formulations include kerosene, fuel oil, xylene, petroleum fractions with boiling ranges above xylene, and aromatic petroleum fractions rich in methylated naphthalenes.

Emulsifiable concentrates consist of an oil solution of the active compound along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate if desired.

What is claimed:

1. A compound having the structural formula

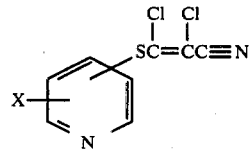

wherein X is selected from the group consisting of —H, —Br, —Cl, —F, methyl, ethyl, propyl and butyl.

2. The compound of claim 1 wherein X is —H.

3. A biocidal composition for control of bacteria, fungi and algae comprising a biocidally effective amount of
   a. a compound having the structural formula

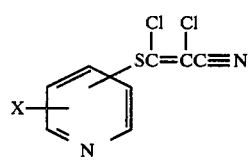

wherein X is selected from the group consisting of —H, —Br, —Cl, —F, methyl, ethyl, propyl and butyl; and
   b. an inert carrier.

4. The biocidal composition of claim 3 wherein X is —H.

5. A method for the control of bacteria, fungi and algae comprising applying to the locus of said bacteria, fungi and algae a biocidally effective amount of a compound having the structural formula

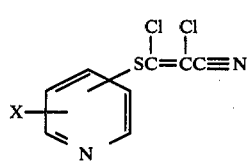

wherein X is selected from the group consisting of —H, —Br, —Cl, —F, methyl, ethyl, propyl and butyl.

6. The method of claim 5 wherein X is —H.

* * * * *